United States Patent
Kensey et al.

(10) Patent No.: US 6,692,437 B2
(45) Date of Patent: Feb. 17, 2004

(54) METHOD FOR DETERMINING THE VISCOSITY OF AN ADULTERATED BLOOD SAMPLE OVER PLURAL SHEAR RATES

(75) Inventors: Kenneth Kensey, Malvern, PA (US); Young Cho, Cherry Hill, NJ (US)

(73) Assignee: Rheologics, Inc., Exton, PA (US)

( * ) Notice: Subject to any disclaimer, the term of this patent is extended or adjusted under 35 U.S.C. 154(b) by 233 days.

(21) Appl. No.: 09/940,372

(22) Filed: Aug. 28, 2001

(65) Prior Publication Data

US 2003/0036711 A1 Feb. 20, 2003

Related U.S. Application Data

(63) Continuation-in-part of application No. 09/573,267, filed on May 18, 2000, now Pat. No. 6,402,703, which is a continuation-in-part of application No. 09/439,795, filed on Nov. 12, 1999, now Pat. No. 6,322,524.

(51) Int. Cl.[7] ............................ A61B 5/00; G01N 11/00
(52) U.S. Cl. ...................... 600/300; 600/368; 600/573; 73/54.01
(58) Field of Search ................................. 600/300, 368, 600/369; 73/54.01, 54.09, 54.12, 54.17, 54.43

(56) References Cited

U.S. PATENT DOCUMENTS

| | | | |
|---|---|---|---|
| 3,720,097 A | * 3/1973 | Kron | 73/54.43 |
| 4,858,127 A | * 8/1989 | Kron et al. | 73/54.09 |
| 5,792,660 A | * 8/1998 | Spillert et al. | 73/54.01 |
| 6,019,735 A | 2/2000 | Kensey et al. | |
| 6,077,234 A | 6/2000 | Kensey | |
| 6,152,888 A | 11/2000 | Kensey et al. | |
| 6,193,667 B1 | 2/2001 | Kensey | |
| 6,200,277 B1 | 3/2001 | Kensey | |
| 6,261,244 B1 | 7/2001 | Kensey et al. | |
| 6,322,524 B1 | 11/2001 | Kensey et al. | |
| 6,322,525 B1 | 11/2001 | Kensey et al. | |
| 6,402,703 B1 | 6/2002 | Kensey et al. | |
| 6,412,336 B2 | 7/2002 | Shin et al. | |
| 6,428,488 B1 | 8/2002 | Kensey et al. | |
| 6,443,911 B1 | 9/2002 | Kensey et al. | |
| 6,450,974 B1 | 9/2002 | Kim et al. | |
| 6,484,565 B2 | 11/2002 | Shin et al. | |
| 6,484,566 B1 | 11/2002 | Shin et al. | |

* cited by examiner

*Primary Examiner*—Max F. Hindenburg
*Assistant Examiner*—David J. McCrosky
(74) *Attorney, Agent, or Firm*—Caesar, Rivise, Bernstein, Cohen & Pokotilow, Ltd.

(57) ABSTRACT

A method for obtaining the viscosity of the circulating blood of a living being using an adulterated blood sample and a correlation factor obtained from a circulating blood viscometer.

3 Claims, 15 Drawing Sheets

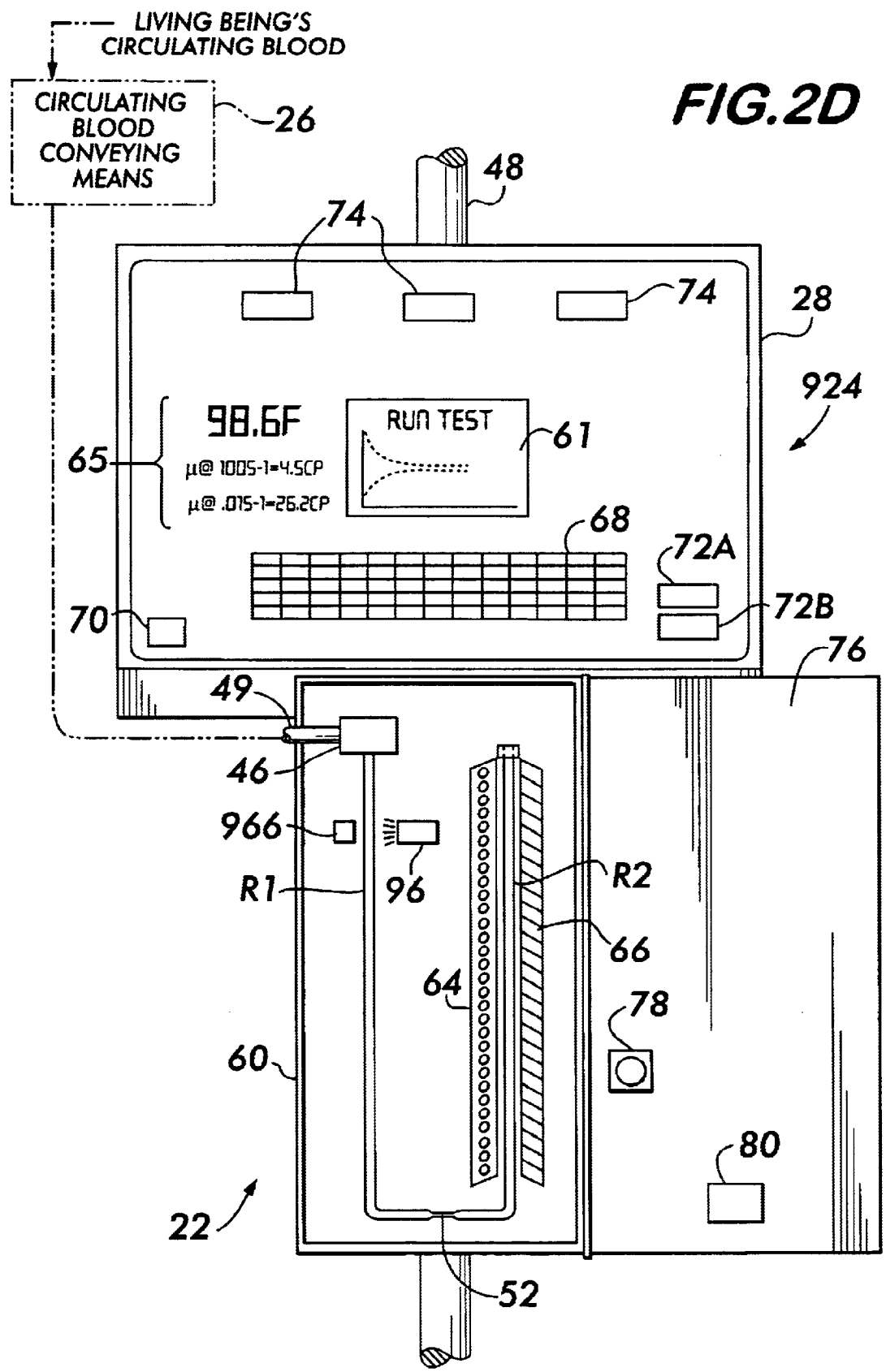

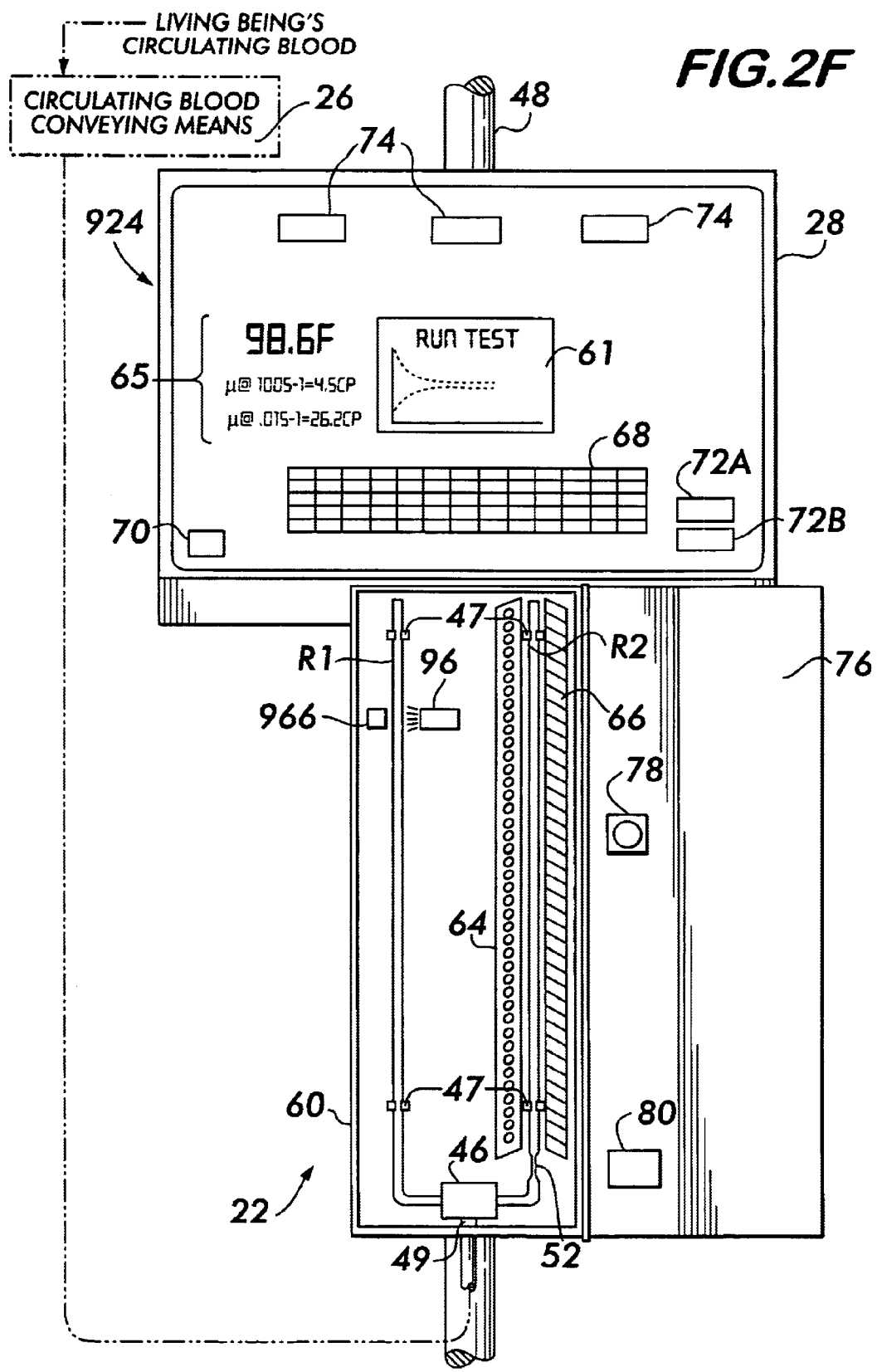

METHOD FOR DETERMINING THE VISCOSITY OF AN ADULTERATED BLOOD SAMPLE OVER PLURAL SHEAR RATES

RELATED APPLICATIONS

This application is Continuation-in-Part of application Ser. No. 09/573,267 (now U.S. Pat. No. 6,402,703), filed on May 18, 2000, which in turn is a Continuation-in-Part of application Ser. No. 09/439,795 (now U.S. Pat. No. 6,322,524), filed Nov. 12, 1999 both of which are entitled DUAL RISER/SINGLE CAPILLARY VISCOMETER and both of whose entire disclosures are incorporated by reference herein and both of which are assigned to the same Assignee as the present invention, namely Visco Technologies, Inc.

FIELD OF THE INVENTION

The invention pertains to methods and apparatus for determining blood viscosity, and more particularly, to a method for obtaining the viscosity of the circulating blood of a living being using an adulterated blood sample and a correlation factor obtained from a circulating blood viscometer.

BACKGROUND OF INVENTION

The importance of determining the viscosity of blood is well-known. *Fibrogen. Viscosity and White Blood Cell Count Are Major Risk Factors for Ischemic Heart Disease*, by Yarnell et al., Circulation, Vol. 83, No. 3, March 1991; *Postprandial Changes in Plasma and Serum Viscosity and Plasma Lipids and Lipoproteins After an Acute Test Meal*, by Tangney, et al., American Journal for Clinical Nutrition, 65:36–40, 1997; *Studies of Plasma Viscosity in Primary Hyperlipoproteinaemia*, by Leonhardt et al., Atherosclerosis 28,29–40, 1977; *Effects of Lipoproteins on Plasma Viscosity*, by Seplowitz, et al., Atherosclerosis 38, 89–95, 1981; *Hyperviscosity Syndrome in a Hypercholesterolemic Patient with Primary Biliary Cirrhosis*, Rosenson, et al., Gastroenterology, Vol. 98, No. 5, 1990; *Blood Viscosity and Risk of Cardiovascular Events:the Edinburgh Artery Study*, by Lowe et al., British Journal of Hematology, 96,168–171, 1997; *Blood Rheology Associated with Cardiovascular Risk Factors and Chronic Cardiovascular Diseases: Results of an Epidemiologic Cross-Sectional Study*, by Koenig, et al., Angiology, The Journal of Vascular Diseases, November 1988; *Importance of Blood Viscoelasticity in Arteriosclerosis*, by Hell, et al., Angiology, The Journal of Vascular Diseases, June, 1989; *Thermal Method for Continuous Blood-Velocity Measurements in Large Blood Vessels, and Cardiac-Output Determination*, by Delanois, Medical and Biological Engineering, Vol. 11, No. 2, March 1973; *Fluid Mechanics in Atherosclerosis*, by Nerem, et al., Handbook of Bioengineering, Chapter 21, 1985.

Much effort has been made to develop apparatus and methods for determining the viscosity of blood. *Theory and Design of Disposable Clinical Blood Viscometer*, by Litt et al., Biorheology, 25, 697–712, 1988; *Automated Measurement of Plasma Viscosity by Capillary Viscometer*, by Cooke, et al., Journal of Clinical Pathology 41, 1213–1216, 1988; *A Novel Computerized Viscometer/Rheometer* by Jimenez and Kostic, Rev. Scientific Instruments 65, Vol 1, January 1994; *A New Instrument for the Measurement of Plasma-Viscosity*, by John Harkness, The Lancet, pp. 280–281, Aug. 10, 1963; *Blood Viscosity and Raynaud's Disease*, by Pringle, et al., The Lancet, pp. 1086–1089, May 22, 1965; *Measurement of Blood Viscosity Using a Conicylindrical Viscometer*, by Walker et al., Medical and Biological Engineering, pp. 551–557, September 1976.

One reference, namely, *The Goldman Algorithm Revisited: Prospective Evaluation of a Computer-Derived Algorithm Versus Unaided Physician Judgment in Suspected Acute Myocardial Infarction*, by Qamar, et al., Am Heart J 138(4):705–709, 1999, discusses the use of the Goldman algorithm for providing an indicator to acute myocardial infarction. The Goldman algorithm basically utilizes facts from a patient's history, physical examination and admission (emergency room) electrocardiogram to provide an AMI indicator.

In addition, there are a number of patents relating to blood viscosity measuring apparatus and methods. See for example, U.S. Pat. Nos. 3,342,063 (Smythe et al.); 3,720,097 (Kron); 3,999,538 (Philpot, Jr.); 4,083,363 (Philpot); 4,149,405 (Ringrose); 4,165,632 (Weber, et. al.); 4,517,830 (Gunn, deceased, et. al.); 4,519,239 (Kiesewetter, et. al.); 4,554,821 (Kiesewetter, et. al.); 4,858,127 (Kron, et. al.); 4,884,577 (Merrill); 4,947,678 (Hori et al.); 5,181,415 (Esvan et al.); 5,257,529 (Taniguchi et al.); 5,271,398 (Schlain et al.); and 5,447,440 (Davis, et. al.).

The Smythe '063 patent discloses an apparatus for measuring the viscosity of a blood sample based on the pressure detected in a conduit containing the blood sample. The Kron '097 patent discloses a method and apparatus for determining the blood viscosity using a flowmeter, a pressure source and a pressure transducer. The Philpot '538 patent discloses a method of determining blood viscosity by withdrawing blood from the vein at a constant pressure for a predetermined time period and from the volume of blood withdrawn. The Philpot '363 patent discloses an apparatus for determining blood viscosity using a hollow needle, a means for withdrawing and collecting blood from the vein via the hollow needle, a negative pressure measuring device and a timing device. The Ringrose '405 patent discloses a method for measuring the viscosity of blood by placing a sample of it on a support and directing a beam of light through the sample and then detecting the reflected light while vibrating the support at a given frequency and amplitude. The Weber '632 patent discloses a method and apparatus for determining the fluidity of blood by drawing the blood through a capillary tube measuring cell into a reservoir and then returning the blood back through the tube at a constant flow velocity and with the pressure difference between the ends of the capillary tube being directly related to the blood viscosity. The Gunn '830 patent discloses an apparatus for determining blood viscosity that utilizes a transparent hollow tube, a needle at one end, a plunger at the other end for creating a vacuum to extract a predetermined amount and an apertured weight member that is movable within the tube and is movable by gravity at a rate that is a function of the viscosity of the blood. The Kiesewetter '239 patent discloses an apparatus for determining the flow shear stress of suspensions, principally blood, using a measuring chamber comprised of a passage configuration that simulates the natural microcirculation of capillary passages in a being. The Kiesewetter '821 patent discloses another apparatus for determining the viscosity of fluids, particularly blood, that includes the use of two parallel branches of a flow loop in combination with a flow rate measuring device for measuring the flow in one of the branches for determining the blood viscosity. The Kron '127 patent discloses an apparatus and method for determining blood viscosity of a blood sample over a wide range of shear rates. The Merrill '577 patent discloses an apparatus and method for determining the blood viscosity of a blood sample using a hollow column in fluid communication with a chamber containing a porous bed and means for measuring the blood flow rate within the column.

The Hori '678 patent discloses a method for measurement of the viscosity change in blood by disposing a temperature sensor in the blood flow and stimulating the blood so as to cause a viscosity change. The Esvan '415 patent discloses an apparatus that detects the change in viscosity of a blood sample based on the relative slip of a drive element and a driven element, which holds the blood sample, that are rotated. The Taniguchi '529 patent discloses a method and apparatus for determining the viscosity of liquids, e.g., a blood sample, utilizing a pair of vertically-aligned tubes coupled together via fine tubes while using a pressure sensor to measure the change of an internal tube pressure with the passage of time and the change of flow rate of the blood. The Bedingham '328 patent discloses an intravascular blood parameter sensing system that uses a catheter and probe having a plurality of sensors (e.g., an $O_2$ sensor, $CO_2$ sensor, etc.) for measuring particular blood parameters in vivo. The Schlain '398 patent discloses a intra-vessel method and apparatus for detecting undesirable wall effect on blood parameter sensors and for moving such sensors to reduce or eliminate the wall effect. The Davis '440 patent discloses an apparatus for conducting a variety of assays that are responsive to a change in the viscosity of a sample fluid, e.g., blood.

Viscosity measuring methods and devices for fluids in general are well-known. See for example, U.S. Pat. Nos. 1,810,992 (Dallwitz-Wegner); 2,343,061 (Irany); 2,696,734 (Brunstrum et al.); 2,700,891 (Shafer); 2,934,944 (Eolkin); 3,071,961 (Heigl et al.); 3,116,630 (Piros); 3,137,161 (Lewis et al.); 3,138,950 (Welty et al.); 3,277,694 (Cannon et al.); 3,286,511 (Harkness); 3,435,665 (Tzentis); 3,520,179 (Reed); 3,604,247 (Gramain et al.); 3,666,999 (Moreland, Jr. et al.); 3,680,362 (Geerdes et al.); 3,699,804 (Gassmann et al.); 3,713,328 (Aritomi); 3,782,173 (Van Vessem et al.); 3,864,962 (Stark et al.); 3,908,441 (Virloget); 3,952,577 (Hayes et al.); 3,990,295 (Renovanz et al.); 4,149,405 (Ringrose); 4,302,965 (Johnson et al.); 4,426,878 (Price et al.); 4,432,761 (Dawe); 4,616,503 (Plungis et al.); 4,637,250 (Irvine, Jr. et al.); 4,680,957 (Dodd); 4,680,958 (Ruelle et al.); 4,750,351 (Ball); 4,856,322 (Langrick et al.); 4,899,575 (Chu et al.); 5,142,899 (Park et al.); 5,222,497 (Ono); 5,224,375 (You et al.); 5,257,529 (Taniguchi et al.); 5,327,778 (Park); and 5,365,776 (Lehmann et al.).

The following U.S. patents disclose viscosity or flow measuring devices, or liquid level detecting devices using optical monitoring: U.S. Pat. Nos. 3,908,441 (Virloget); 5,099,698 (Kath, et. al.); 5,333,497 (Br nd Dag A. et al.). The Virloget '441 patent discloses a device for use in viscometer that detects the level of a liquid in a transparent tube using photodetection. The Kath '698 patent discloses an apparatus for optically scanning a rotameter flow gauge and determining the position of a float therein. The Br nd Dag A. '497 patent discloses a method and apparatus for continuous measurement of liquid flow velocity of two risers by a charge coupled device (CCD) sensor.

U.S. Pat. No. 5,421,328 (Bedingham) discloses an intravascular blood parameter sensing system.

A statutory invention registration, H93 (Matta et al.) discloses an apparatus and method for measuring elongational viscosity of a test fluid using a movie or video camera to monitor a drop of the fluid under test.

The following publications discuss red blood cell deformability and/or devices used for determining such: *Measurement of Human Red Blood Cell Deformability Using a Single Micropore on a Thin $Si_3N_4$ Film*, by Ogura et al, IEEE Transactions on Biomedical Engineering, Vol. 38, No. 8, August 1991; *the Pall BPF4 High Efficiency Leukocyte Removal Blood Processing Filter System*, Pall Biomedical Products Corporation, 1993.

A device called the "Hevimet 40" has recently been advertised at www.hevimet.freeserve.co.uk. The Hevimet 40 device is stated to be a whole blood and plasma viscometer that tracks the meniscus of a blood sample that falls due to gravity through a capillary. While the Hevimet 40 device may be generally suitable for some whole blood or blood plasma viscosity determinations, it appears to exhibit several significant drawbacks. For example, among other things, the Hevimet 40 device appears to require the use of anticoagulants. Moreover, this device relies on the assumption that the circulatory characteristics of the blood sample are for a period of 3 hours the same as that for the patient's circulating blood. That assumption may not be completely valid.

In contrast, the recent development of circulating blood viscometers by the Assignee, namely Visco Technologies, Inc., of Exton, Pa., of the present invention whereby the circulating blood of a living being is subjected to a plurality of shear rates that can be easily detected and without the need to adulterate the blood, permits a more accurate and quick method for determining the blood viscosity.

However, there still remains a need for using conventional blood viscometers in conjunction with these circulating blood viscometers to obtain the same accurate results, even where these conventional blood viscometers use an adulterated blood sample.

SUMMARY OF THE INVENTION

A method for determining the viscosity of the circulating blood of a living being using an adulterated blood sample from the living being. The method comprises the steps of: (a) dividing the population of living beings into a plurality of categories; (b) selecting a predetermined number of living beings in each of the categories and obtaining a first blood viscosity vs. shear rate profile for each of the living beings using a circulating blood viscometer (e.g., a dual riser/single capillary viscometer, a single riser/single capillary viscometer using mass detection or column height detection, etc.); (c) obtaining a blood sample from each of said predetermined number of living beings and then adulterating each of the blood samples; (d) inputting each of said adulterated blood samples into a conventional blood viscometer (e.g., a cone and plate viscometer, etc.) and obtaining a second blood viscosity vs. shear rate profile; (e) comparing the first blood viscosity vs. shear rate profile to the second blood viscosity vs. shear rate profile for each of the blood samples to determine a correlation factor, $y_{cf}$, for each of the living beings in each one of the plurality of categories; (f) determining an average correlation factor, $y_{cf}$, for each one of the plurality of categories from the correlation factors, $y_{cf}$, in each one of the plurality of categories, and wherein the average correlation factor, $y_{cf}$, is applied to any subsequent blood viscosity vs. shear rate profile obtained from a conventional blood viscometer to obtain the circulating blood viscosity.

DESCRIPTION OF THE DRAWINGS

FIG. 2D is a front view of an embodiment of the DRSC viscometer of FIG. 2C;

FIG. 2F is a front view of an embodiment of the DRSC viscometer of FIG. 2E;

DETAILED DESCRIPTION OF THE PREFERRED EMBODIMENTS

The method 1320 (FIG. 5) of the present invention involves utilizing "circulating blood viscometers" which are owned by Visco Technologies, Inc. of Exton, Pa. Examples of circulating blood viscometers are the subject matter of the following U.S. patent applications:

application Ser. No. 09/439,795: Dual Riser/Single Capillary Viscometer;

Application Ser. No. 09/897,176 (now U.S. Pat. No. 6,412,336) filed on Jul. 2, 2001 entitled: Single Riser/Single Capillary Blood Viscometer Using Mass Detection or Column Height Detection; and Application Ser. No. 09/908,374 filed on Jul. 18, 2001 entitled: Single Capillary Tube Viscometer As referred to throughout this Specification, circulating blood viscometers operate by immediately diverting a portion of the living being's blood into a device that subjects the circulating blood to a plurality of shear rates using a decreasing pressure differential. The device monitors or detects the movement of the circulating blood as it passes through the plurality of shear rates and then from this movement, as well as using known dimensions of the passageways in the device, the viscosity of the circulating blood can be accurately and quickly determined. The diverted blood remains unadulterated throughout the analysis.

Figure 1:
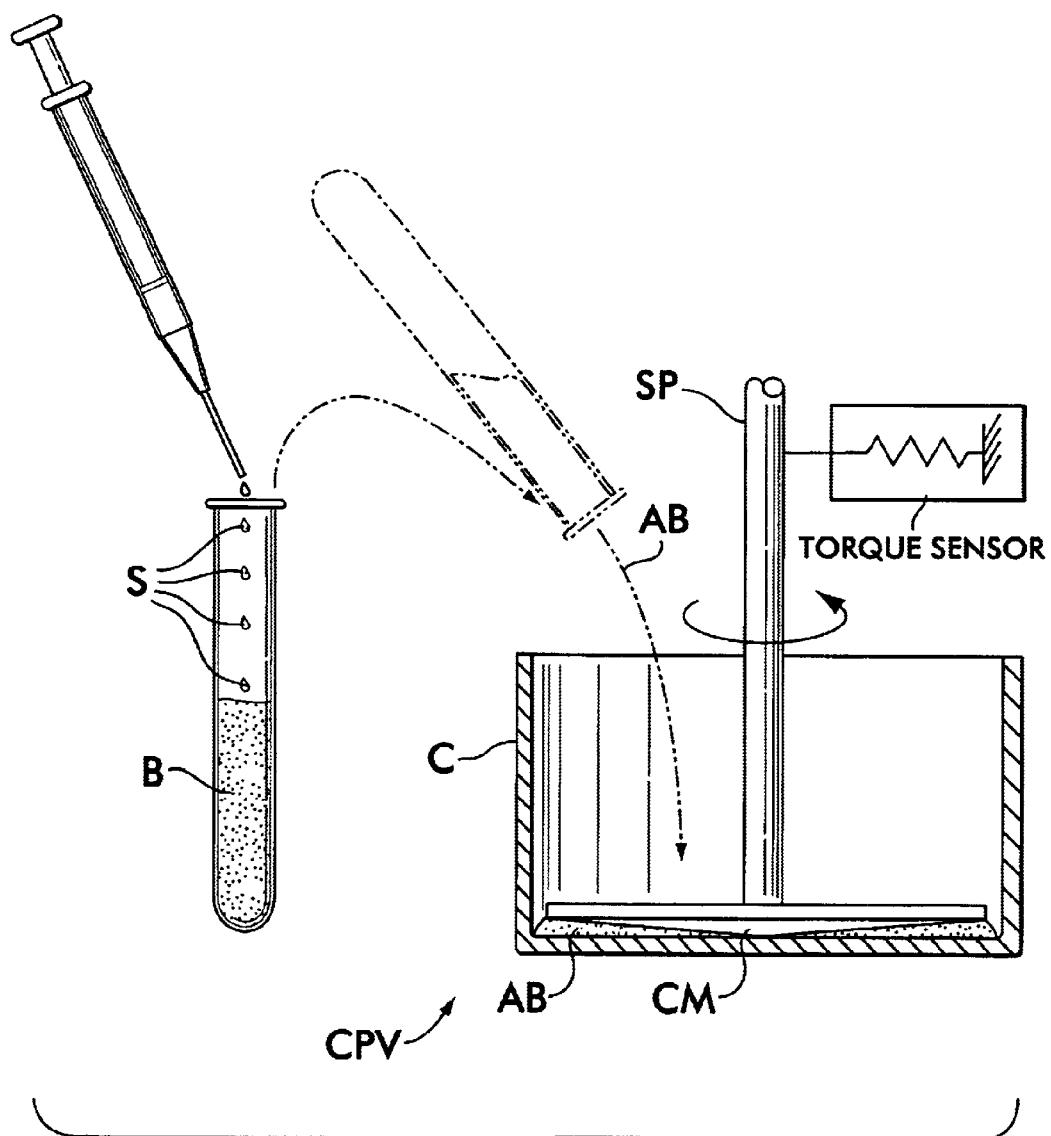
FIG. 1 is a functional diagram of a "cone and plate" viscometer and depicting how an adulterated blood sample is introduced into the cone and plate viscometer.

In contrast, the phrase "conventional blood viscometers" as used throughout this Specification implies viscometers or rheometers that operate by having a blood sample, removed from a living being's bloodstream and adulterated in some manner (e.g., application of anti-coagulant), introduced into, and then analyzed by, the viscometer or rheometer. Although these conventional blood viscometers may place the blood sample through a plurality of shear rates, they do not utilize the circulating blood directly from the living being and usually administer an anti-coagulant in order to conduct the viscosity analysis. One example of a conventional blood viscometer is a "cone and plate" viscometer that is typically used in blood viscosity determination. FIG. 1 is a functional diagram of a cone and plate viscometer, CPV. In particular, a blood sample B is removed from a living being and then the blood sample B is adulterated with a substance S, e.g., an anti-coagulant, a new pharmaceutical, etc. This adulterated blood sample AB is then introduced into the CPV. The CPV basically comprises a coned member CM having a spindle SP and wherein the coned member CM is centrally-located within a collector C. A motor (not shown) rotates the coned member CM which causes the different levels of the adulterated blood sample AB to be sheared at different shear rates. A torque sensor measures the applied torque on the spindle SP. Using the applied torque and the radius (i.e., the moment arm) of the coned member CM, the viscosity of the adulterated blood sample AB is then calculated.

Where access to any of these circulating blood viscometers is limited, the following sets forth a method 1320 whereby a conventional blood viscometer, e.g., a cone and plate viscometer, can be used to obtain the accuracy of blood viscosity determinations made with circulating blood viscometers but without the need to directly use any of the circulating blood viscometers. However, before the method 1320 is discussed, examples of circulating blood viscometers are discussed.

One example of a circulating blood viscometer is the dual riser/single capillary (DRSC) viscometer 20 of application Ser. Nos. 09/573,267 and 09/439,795 which, when used with a sensor and processor, determines the viscosity of the circulating blood of a living being over plural shear rates. FIGS. 2A–2F pertain to the inventions of application Ser. Nos. 09/573,267 and 09/439,795.

The DRSC viscometer basically comprises a U-shaped structure wherein a portion of that U-shaped structure comprises a flow restrictor, e.g., a capillary tube. The DRSC viscometer is arranged to establish two oppositely moving columns of blood which experience a decreasing pressure differential. The movement of at least one of the columns of blood is detected over time (e.g., using a column level detector, a mass detector, etc.). From this data and using the dimensions of the flow restrictor, the viscosity can be determined.

Figure 2A:
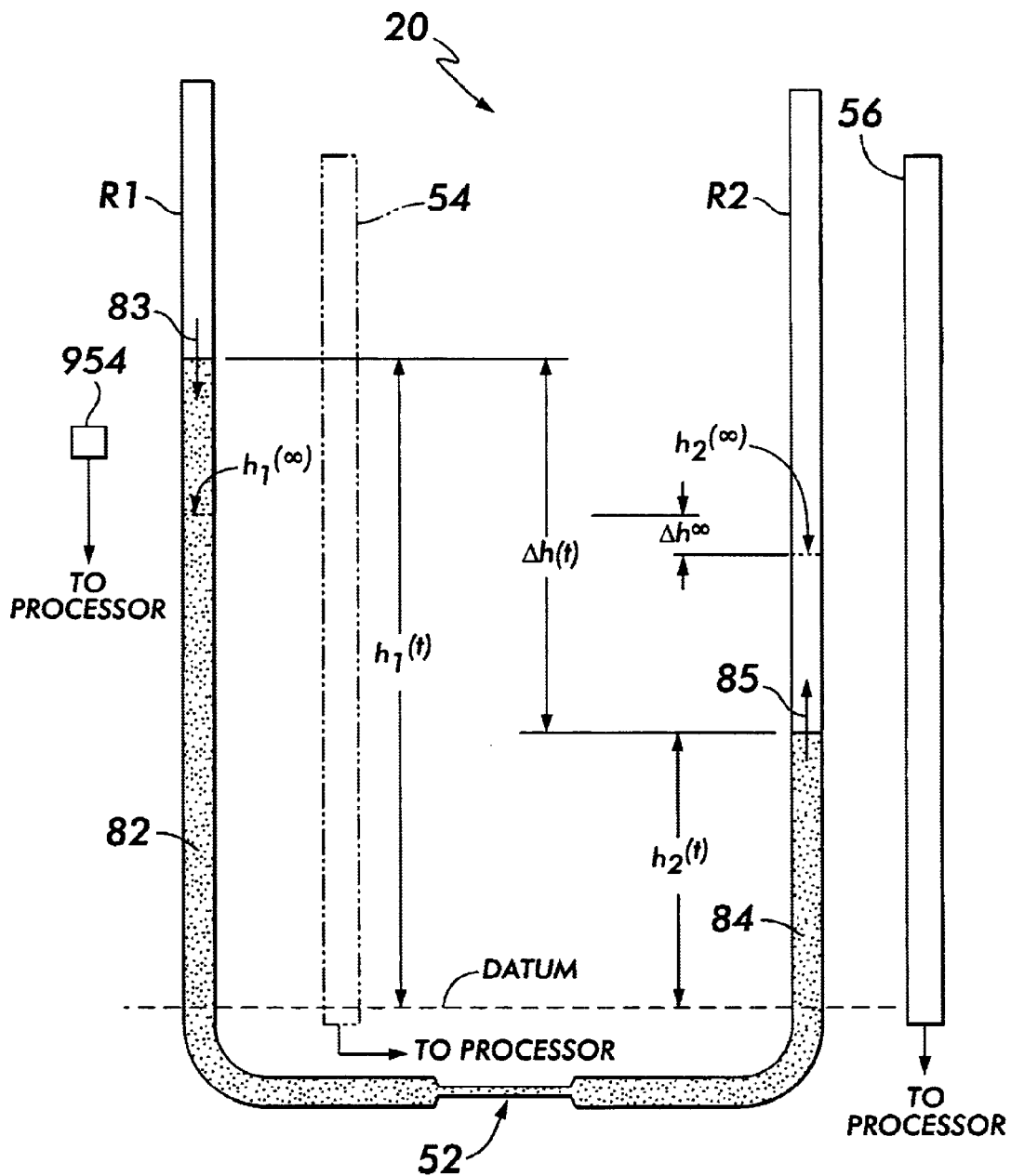
FIG. 2A is a functional diagram of a fluid under test using a dual riser/single capillary (DRSC) viscometer as discussed in application Ser. No. 09/439,735 or Ser. No. 09/573,267.
Figure 2B:
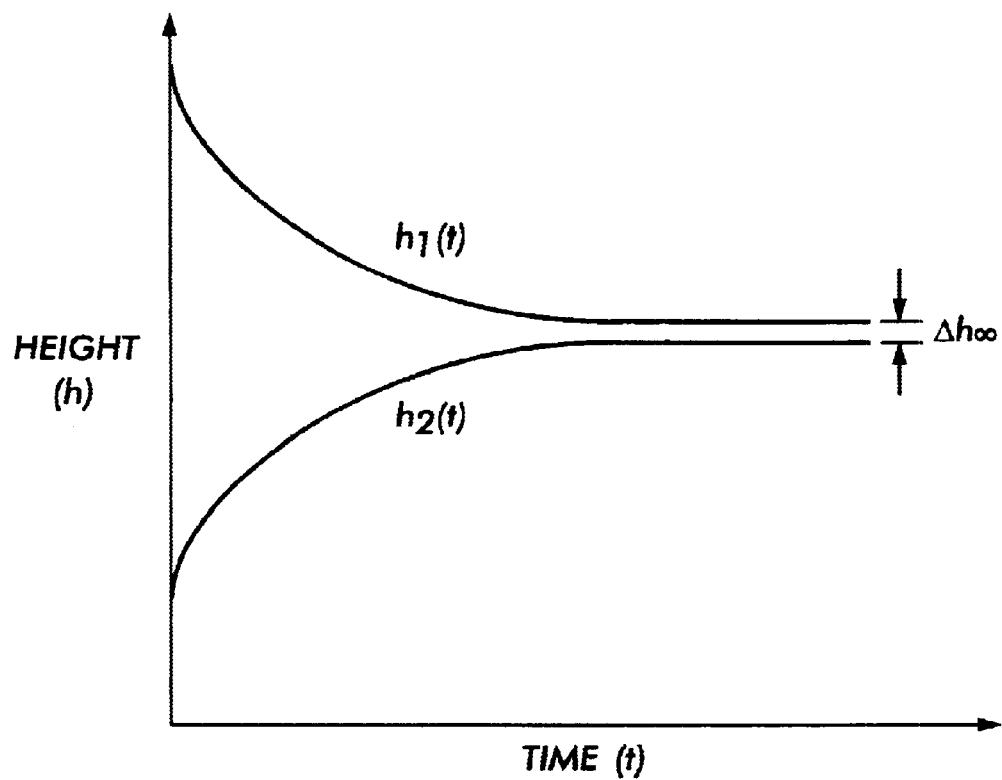
FIG. 2B is a graphical representation of the height of the respective columns of fluid overtime in the two riser tubes of the DRSC viscometer as discussed in application Ser. No. 09/439,735 or Ser. No. 09/573,267.

FIG. 2A depicts the concept of the DRSC viscometer 20 wherein the U-shaped structure comprises a pair of riser tubes, R1 and R2, and a flow restrictor 52. The movement of the columns of blood 82 and 84 in the respective directions 83 and 85 are monitored by respective column level detectors 54 and 56 (application Ser. No. 09/439,795); or alternatively, one of the column level detectors, e.g., 54, can be replaced by a single point detector 954 (application Ser. No. 09/573,267). The sensors generate height data, $h_1(t)$ and $h_2(t)$, over time and provide this data to a computer (not shown). At the end of the viscosity test run, the height of the two columns, namely $h_1(\infty)$ and $h_2(\infty)$, are not equal and the result is a $\Delta h_\infty$, the cause of which may be attributed to surface tension and yield stress of the blood. FIG. 2B depicts a height vs. time plot for each of the columns of blood. The computer calculates the blood viscosity from the height data and the dimensions of the flow restrictor 52. The details of the how the blood viscosity is calculated using the DRSC viscometer 20 is set forth in application Ser. Nos. 09/573,267 and 09/439,795 both of whose entire disclosures are incorporated by reference herein and as a result will not be discussed further.

Figure 2C:
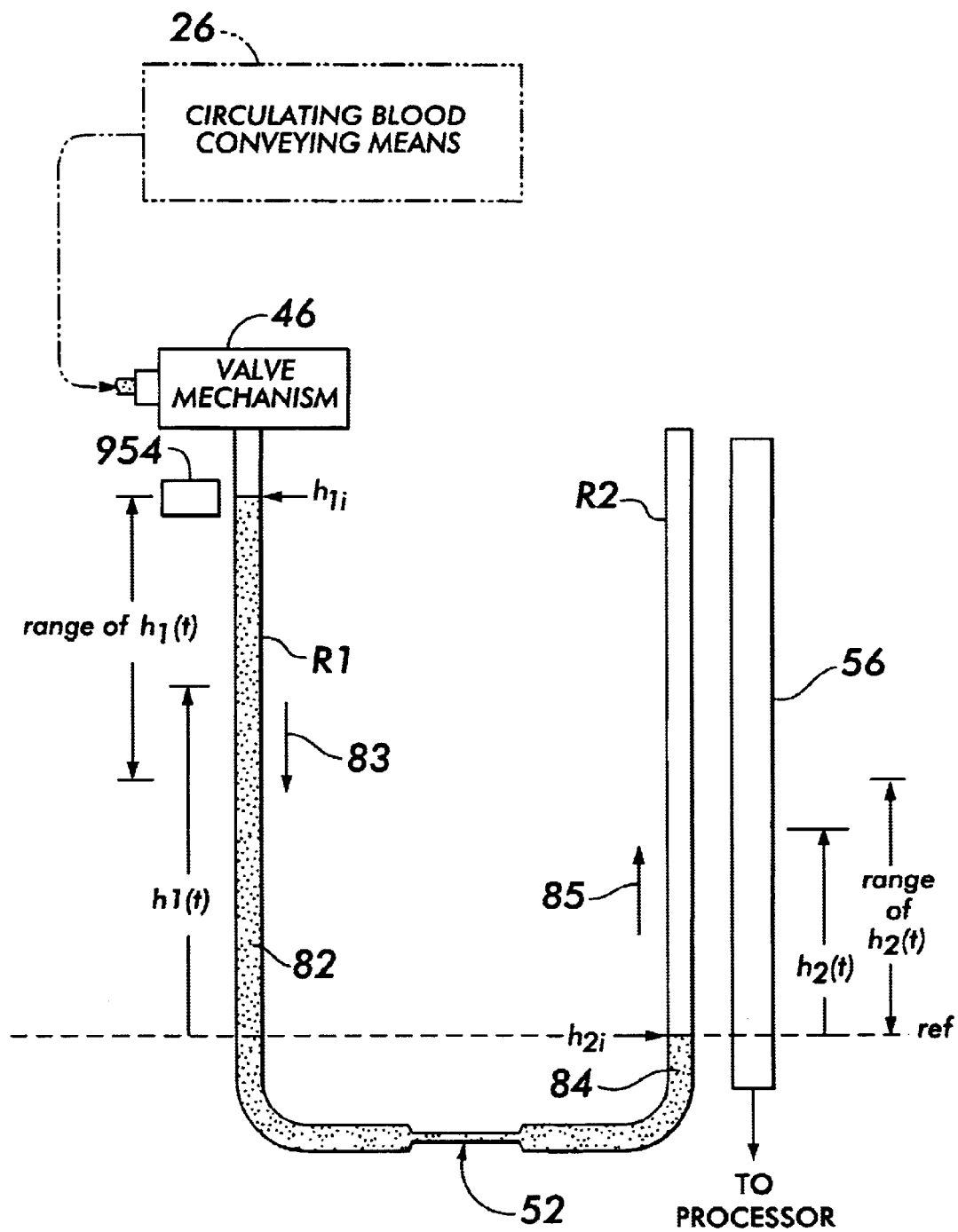
FIG. 2C is a functional diagram of the DRSC viscometer as discussed in application Ser. No. 09/439,735 or Ser. No. 09/573,267 wherein the circulating blood of a living being is the fluid under test.
Figure 2E:
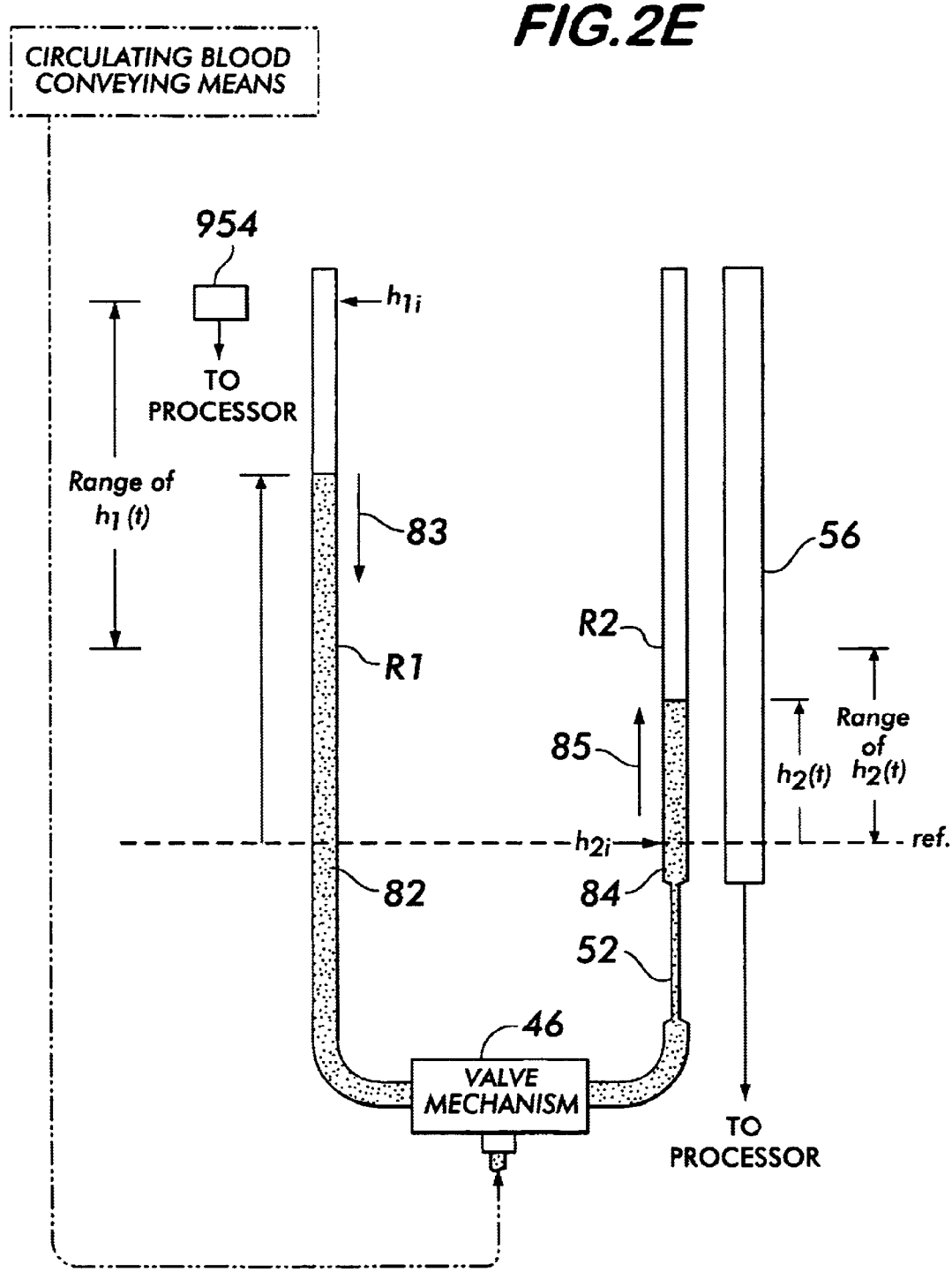
FIG. 2E is an alternative functional diagram of the DRSC viscometer as discussed in application Ser. No. 09/439,735 or Ser. No. 09/573,267 wherein the circulating blood of a living being is the fluid under test.

As also discussed in application Ser. Nos. 09/573,267 and 09/439,795, in order to rapidly generate the oppositely-moving columns of blood from the diverted circulating blood of the living being, a valve mechanism 46 is also utilized with the DRSC viscometer and is controlled by the computer. Depending on where the flow restrictor 52 is positioned in the U-shaped structure, the valve mechanism 46 position is selected. For example, in FIG. 2C, the concept of the DRSC viscometer using a flow restrictor 52 at the base of the U-shaped structure has the valve mechanism 46 positioned at the top of the riser tube R1. An embodiment of the DRSC viscometer of FIG. 2C is depicted in FIG. 2D; the embodiment basically comprises a blood receiving means 22 that houses the U-shaped structure and an analyzer 924 portion that includes the computer and a display screen 28 for providing the operator with viscosity, and other critical, data. An alternative configuration is shown in FIGS. 2E and 2F. FIG. 2E shows the concept of the DRSC viscometer using a flow restrictor 52 as part of one of the riser tubes, e.g., R2, and FIG. 2F is an embodiment of that concept.

It should also be understood that the entire disclosure of application Ser. No. 09/708,137 (now U.S. Pat. No. 6,450,974), filed on Nov. 8, 2000 entitled A METHOD OF ISOLATING SURFACE TENSION & YIELD STRESS IN VISCOSITY MEASUREMENTS, which is assigned to the same Assignee as the present invention, namely, Visco Technologies, Inc., is incorporated by reference herein with regard to the DRSC viscometer 20. In that application, a methodology is disclosed in which the surface tension and yield stress effects of the fluid under test are isolated from the viscosity measurements.

Figure 3A:
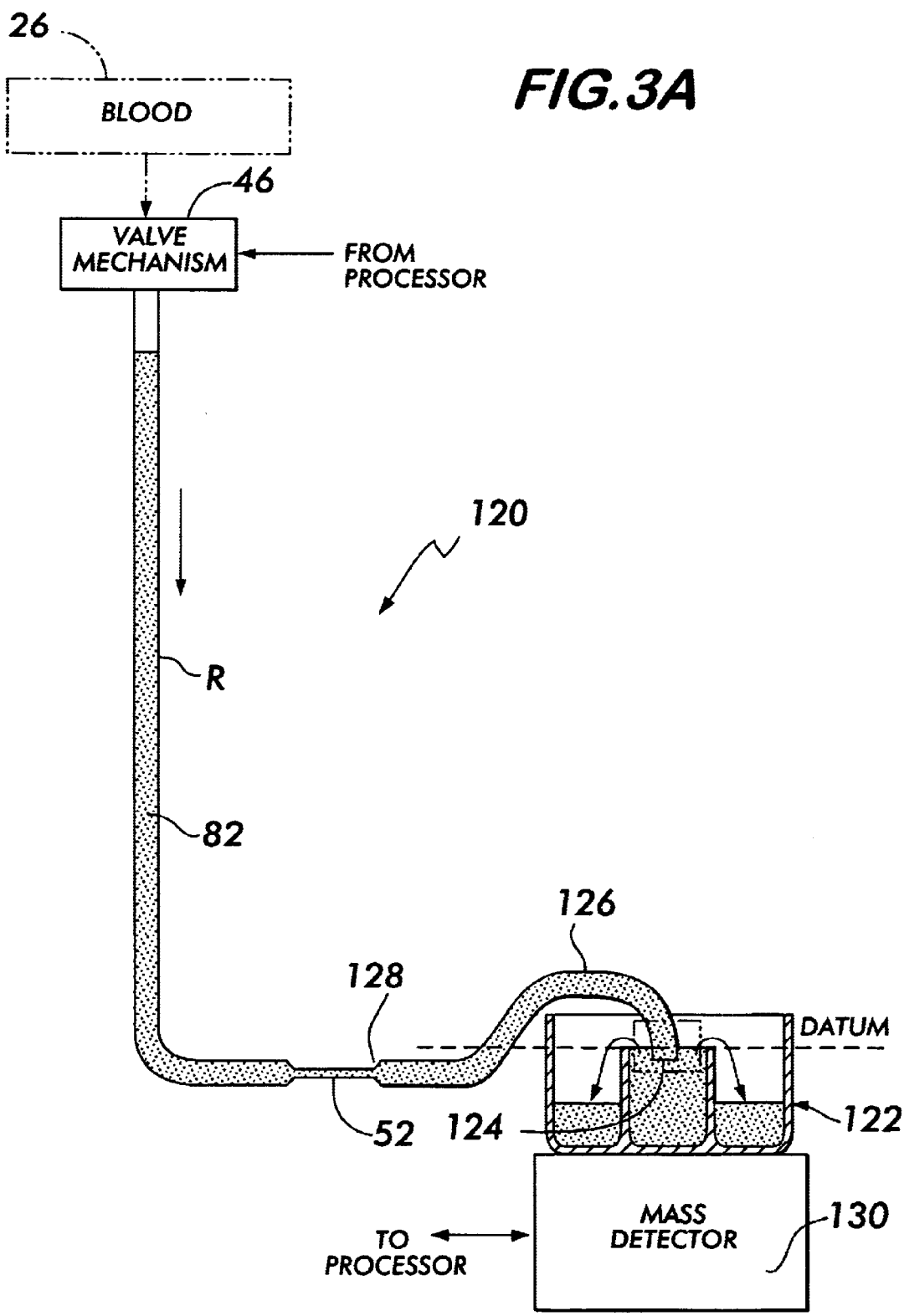
FIG. 3A is a functional diagram of a single riser/single capillary tube viscometer using mass detection.
Figure 3B:
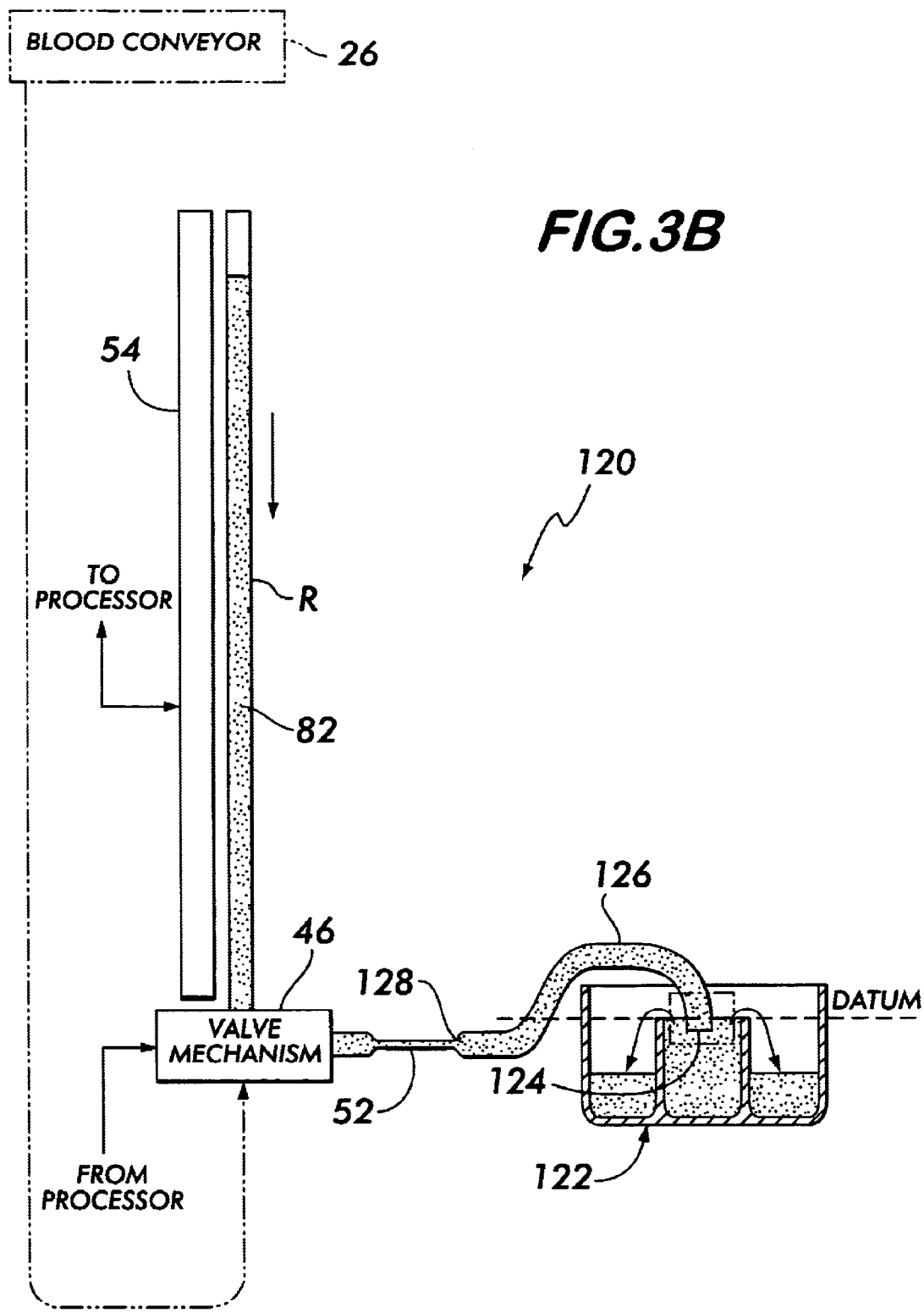
FIG. 3B is a functional diagram of a single riser/single capillary tube viscometer using column height detection.

A second example of a circulating blood viscometer is shown in FIGS. 3A–3B and is known as a single riser/single capillary (SRSC) blood viscometer using mass detection or column height detection and which forms the subject matter of a application Ser. No. 09/897,176 (now U.S. Pat. No. 6,412,336). filed on Jul. 2, 2001 entitled Single Riser/Single Capillary Blood Viscometer Using Mass Detection or Column Height Detection, and whose entire disclosure is incorporated by reference herein. This SRSC blood viscometer 120 utilizes a falling column of blood under the influence of a decreasing pressure differential to detect either the changing mass of the column of blood 82 in a single riser tube R (FIG. 3A) or the changing height of the column of blood 82 (FIG. 3B) as the column moves through a plurality of shear rates. The SRSC blood viscometer 120 utilizes a specialized blood collector 122 which maintains an output end 124 of an adaptor 126 submerged in blood that is collecting in the blood collector 122; this minimizes any surface tension effects that would normally occur if the output 128 of the flow restrictor 52 were simply positioned over the collector 122. In operation, the column of blood 82 falls through a plurality of shear rates under the influence of the decreasing pressure differential which is detected either by a mass detector 130 or the column level detector 54. In accordance with the disclosure set forth in application Ser. No. 09/897,164 (now U.S. Pat. No. 6,484,565), filed on Jul. 2, 2001 entitled Single Riser/Single Capillary Blood Viscometer Using Mass Detection or Column Height Detection, the circulating blood viscosity is then determined from this detected data along with dimensions of the passageways in the device 120.

Figure 4A:
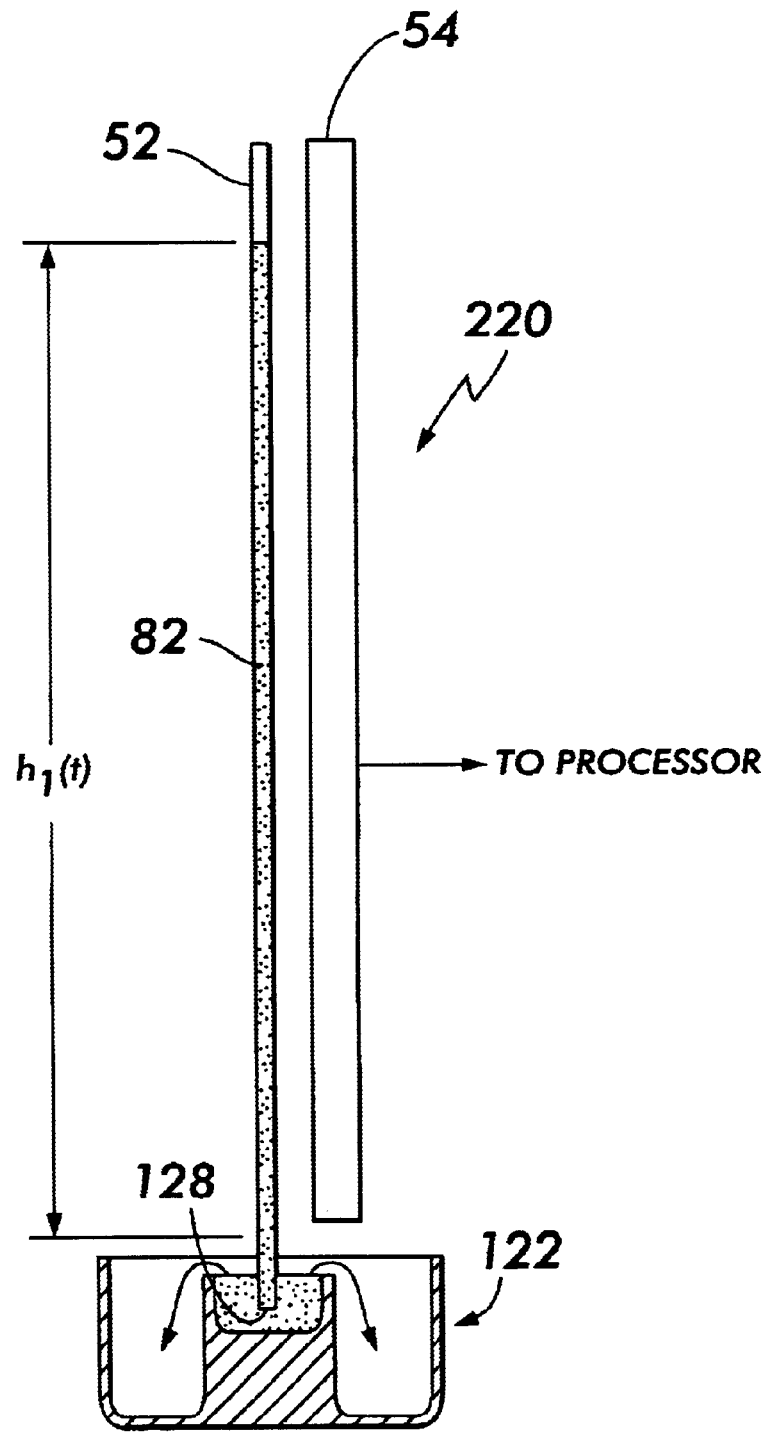
FIG. 4A is a functional diagram of a single capillary tube viscometer.
Figure 4B:
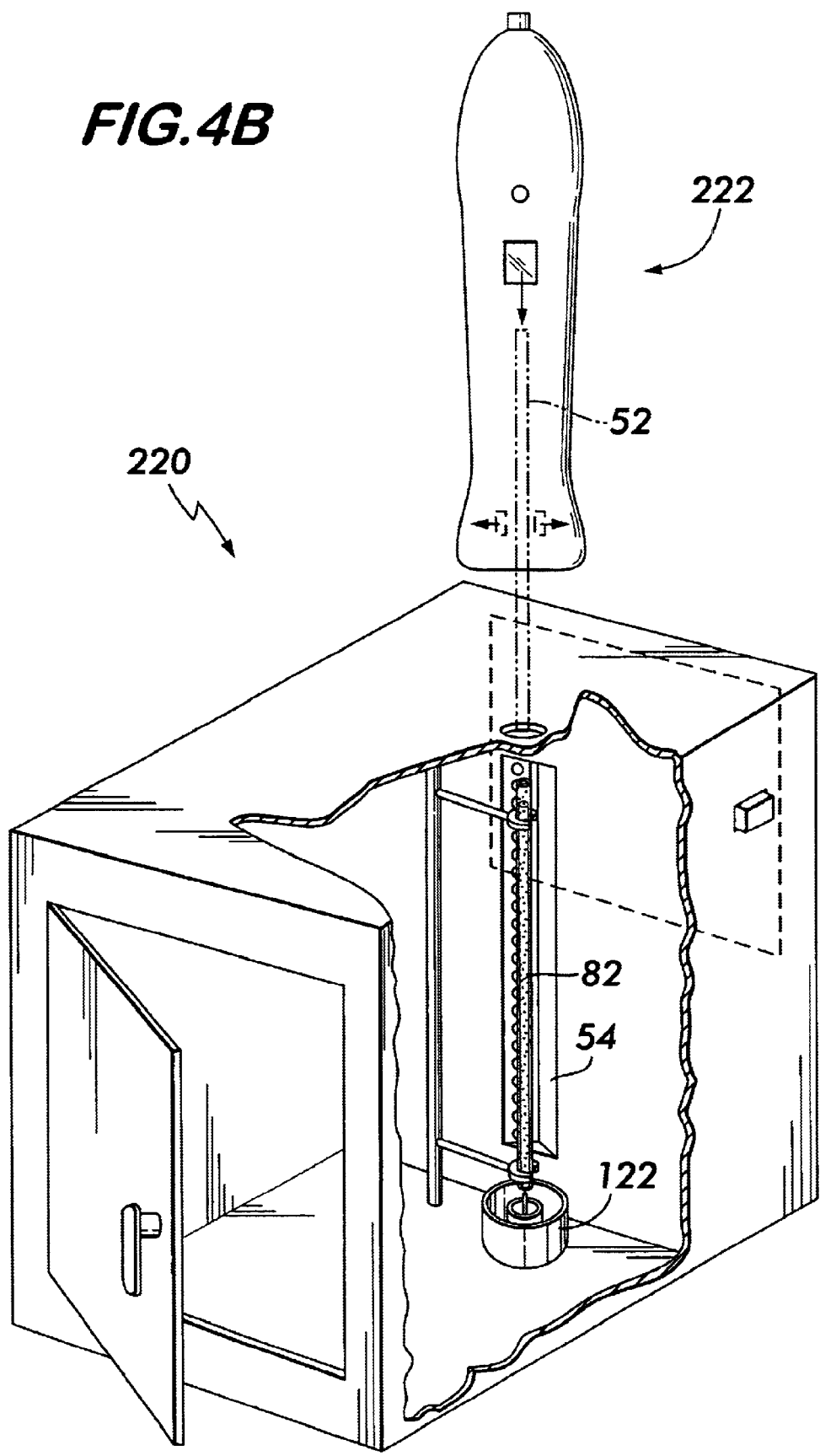
FIG. 4B is an embodiment of the single capillary tube viscometer of FIG. 3A.

A third example of a circulating blood viscometer is shown in FIGS. 4A–4B and is known as a single capillary tube viscometer (SCTV) which forms the subject matter of application Ser. No. 09/908,374, filed on Jul. 18, 2001 entitled "Single Capillary Tube Viscometer", and whose entire disclosure is incorporated by reference herein. This SCTV 220 also utilizes a falling column of blood 82 under the influence of a decreasing pressure differential to detect the changing height of the column of blood 82 as the column moves through a plurality of shear rates. However, this device uses only a capillary tube 52 whose output end 128 is also submerged in blood collecting in the collector 130 to minimize surface tension effects. FIG. 4B depicts an exemplary embodiment of the SCTV 220. In particular, and in accordance with application Ser. No. 09/908,374, filed on Jul. 18, 2001 entitled "Single Capillary Tube Viscometer", the SCTV 120 comprises a hand-held portion 222 and an analyzer portion 224. The hand-held portion 222 initially contains the capillary tube 52 and permits blood to be withdrawn from the living being and into the capillary tube 52. The hand-held portion 222 is then immediately interfaced with the analyzer portion 224 and the filled capillary tube 52 is released into the analyzer portion 224. With the filled capillary tube 52 inserted into the analyzer portion 224, the SCTV 220 is formed (as shown in FIG. 4A) and the blood viscosity analysis begins immediately.

Thus, the above represent exemplary circulating blood viscometers that can be used to determine the viscosity of the circulating blood of a living being over a plurality of shear rates without the need to adulterate the blood. The result is an accurate and quick determination of the circulating blood of the living being.

Figure 5:
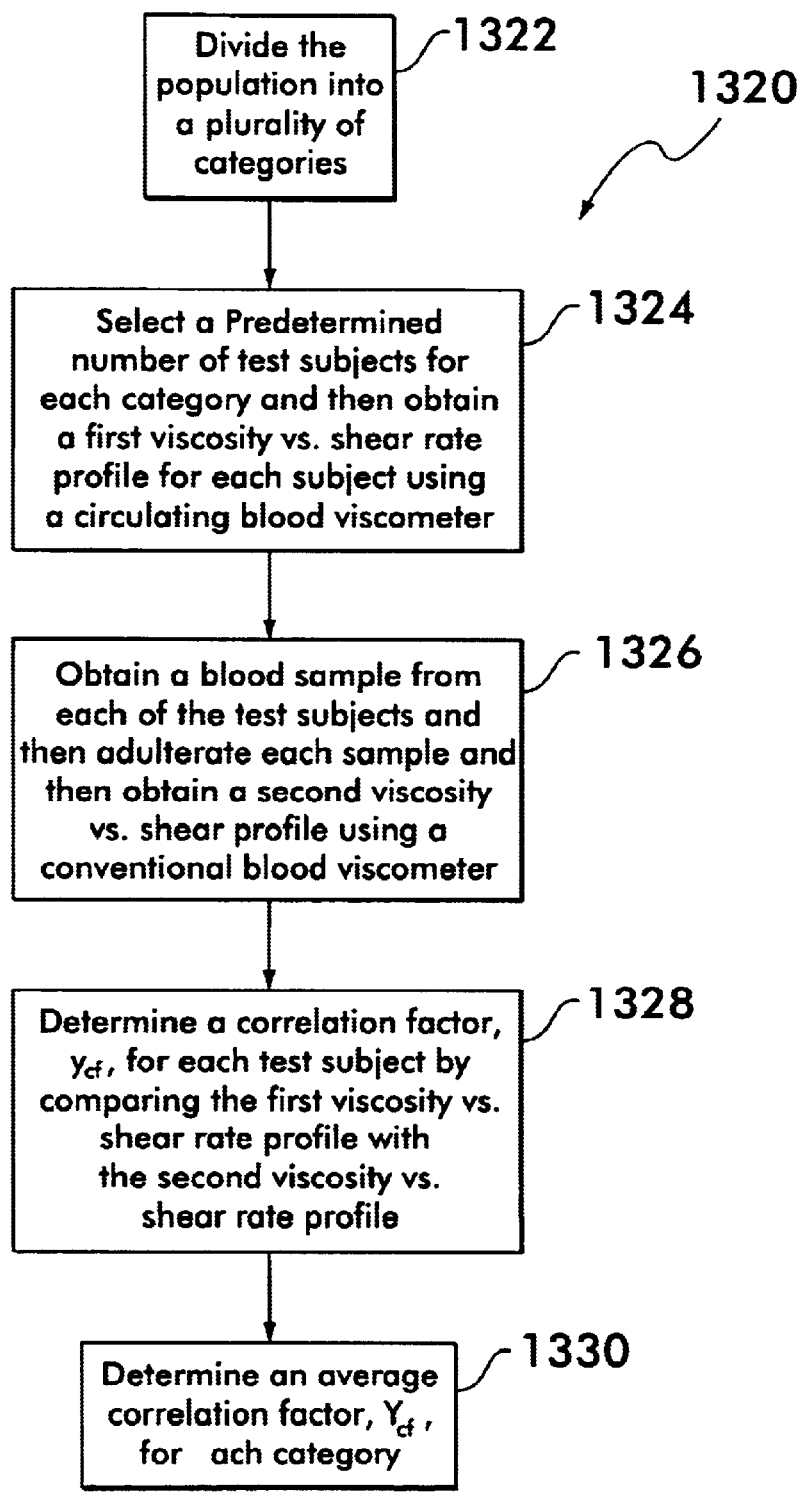
FIG. 5 is a flow diagram of the method of the present invention.
Figure 6:
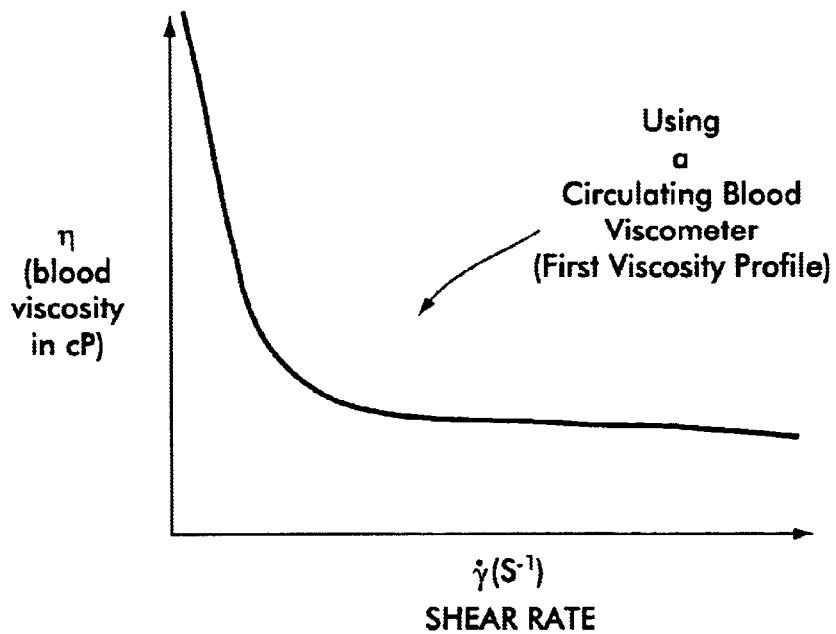
FIG. 6 is a blood viscosity vs. shear rate profile obtained from a circulating blood viscometer and also referred to as the "first viscosity profile"
Figure 7:
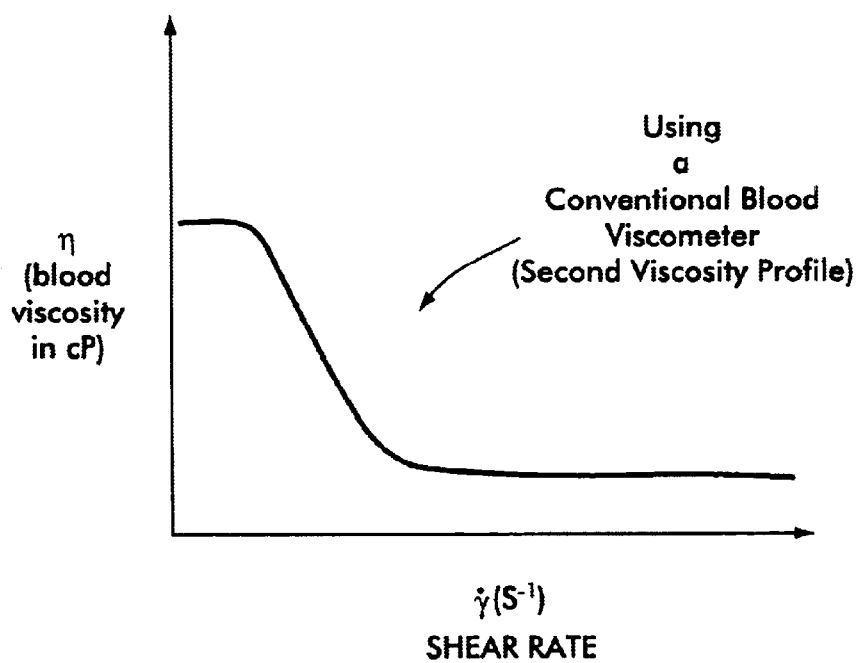
FIG. 7 is another blood viscosity vs. shear rate profile obtained from a conventional blood viscometer and also referred to as the "second viscosity profile"
Figure 8:
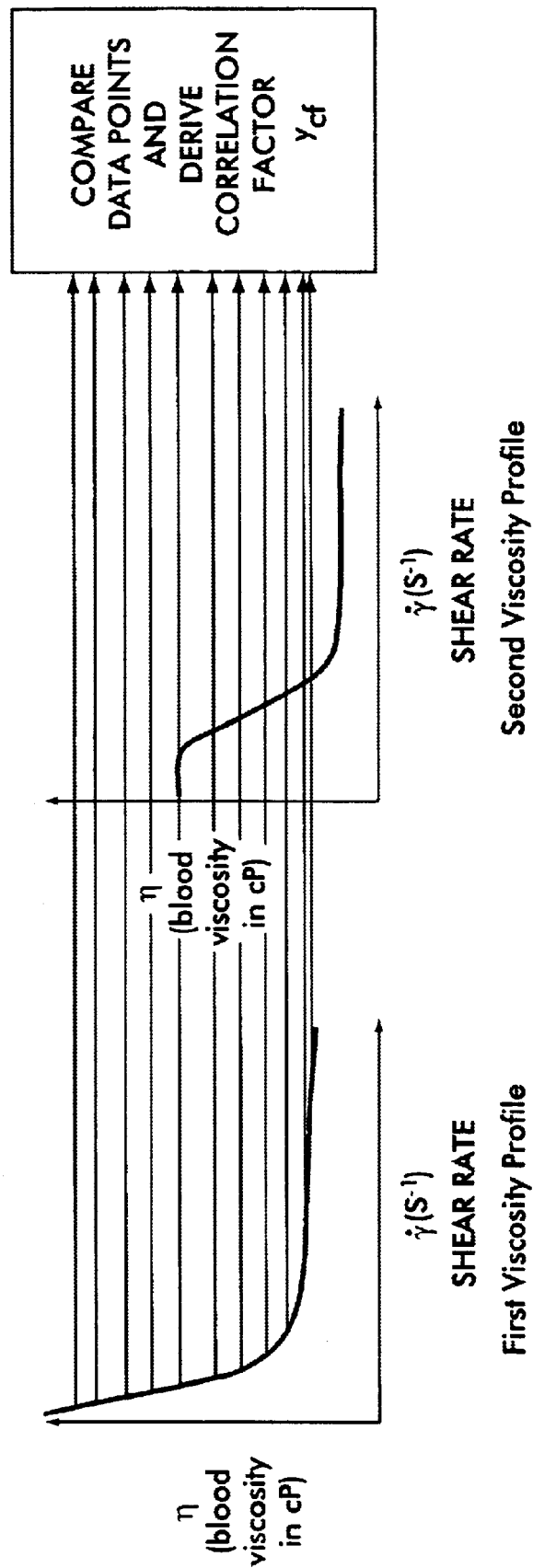
FIG. 8 depicts how the correlation factor, $y_{cf}$, is obtained by comparing the data points of the first and second viscosity profiles.

FIG. 5 depicts the method 1320 for the present invention. Step 1322: divide the population into a plurality of categories, e.g., normal adult male, normal adult female, normal child male, normal child female, diabetic adult male, diabetic adult female, diabetic child male, diabetic child female, adult male smoker, adult female smoker, etc. Step 1324: select a predetermined number, e.g., ten, of subjects in each of the categories and obtain a blood viscosity vs. shear rate profile for each subject using a circulating blood viscometer (e.g., the DRSC viscometer 20, the SRSC blood viscometer 120, the SCTV 220, etc.); this is referred to as a "first viscosity profile" (see FIG. 6). Step 1326: obtain a blood sample from each of the predetermined number of subjects and then adulterate the sample, e.g., administer an anti-coagulant therein. Next, place the adulterated sample into a conventional blood viscometer (e.g., "cone and plate" viscometer), and obtain a second blood viscosity vs. shear rate profile; hereinafter this is referred to as a "second viscosity profile" (FIG. 7). Step 1328: determine a correlation factor, $y_{cf}$, for each subject wherein the correlation factor, $y_{cf}$, when applied to the data points of the second viscosity profile, yield the data points of the first viscosity profile. In particular, the two viscosity profiles are compared, using any well-known statistics program, or other program that can compare data points (see FIG. 8) and can determine a factor relating the data points of the two viscosity profiles such that when the correlation factor, $y_{cf}$ is applied to the data points of the second viscosity profile, the first viscosity profile is obtained. It should be noted that the correlation factor, $y_{cf}$, may comprise a matrix since $y_{cf}=f(\dot{\gamma})$, i.e., since the correlation factor, $y_{cf}$, is a function of the shear rate, $\dot{\gamma}$. Step 1330: determine an average correlation factor, $Y_{cf}$, for each particular group from the test subjects' individual correlation factors.

Figure 9:
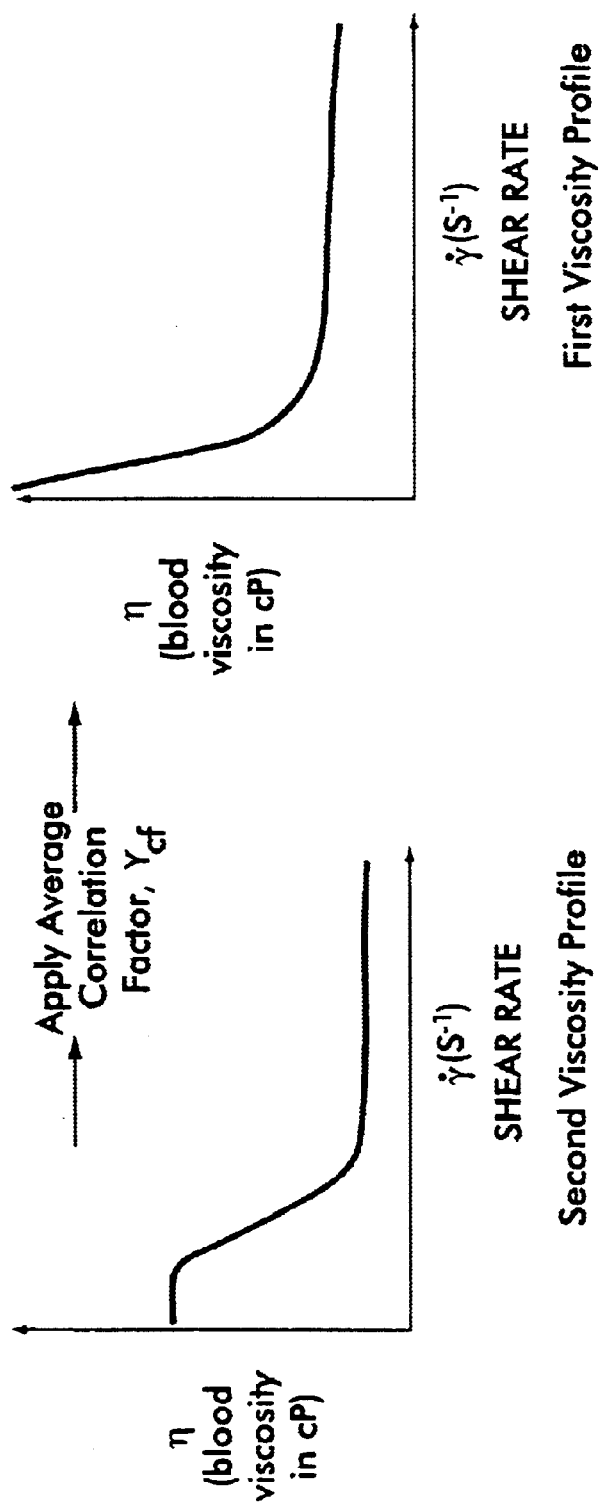
FIG. 9 depicts how the average correlation factor, $y_{cf}$, is applied to the second viscosity profile to obtain the first viscosity profile without the need to use a circulating blood viscometer.

Once this average correlation factor, $Y_{cf}$, is determined for each particular group, the viscosity of the circulating blood of a living being can be obtained using a conventional blood viscometer. In particular, a blood sample is removed from the living being which is then adulterated (e.g., an anticoagulant administered to the sample) and is then placed into the conventional blood viscometer (e.g., cone and plate viscometer). A blood viscosity vs. shear rate profile is then generated. Next, depending into which category the living being can be categorized, the corresponding average correlation factor, $Y_{cf}$, is selected and then applied to the blood viscosity vs. shear rate profile obtained from the conventional blood viscometer. The result is a blood viscosity vs. shear rate profile that would have been obtained had one of the circulating blood viscometers been used directly. See FIG. 9.

Without further elaboration, the foregoing will so fully illustrate our invention that others may, by applying current or future knowledge, readily adopt the same for use under various conditions of service.

We claim:

1. A method for determining the viscosity of the circulating blood of a living being using an adulterated blood sample from the living being, said method comprising the steps of:

(a) dividing the population of living beings into a plurality of categories;

(b) selecting a predetermined number of living beings in each of the categories and obtaining a first blood viscosity vs. shear rate profile for each of the living beings using a circulating blood viscometer;

(c) obtaining a blood sample from each of said predetermined number of living beings and then adulterating each of the blood samples;

(d) inputting each of said adulterated blood samples into a conventional blood viscometer and obtaining a second blood viscosity vs. shear rate profile;

(e) comparing said first blood viscosity vs. shear rate profile to said second blood viscosity vs. shear rate profile for each of said blood samples to determine a correlation factor, $y_{cf}$, for each of the living beings in each one of said plurality of categories;

(f) determining an average correlation factor, $Y_{cf}$, for each one of said plurality of categories from said correlation factors, $y_{cf}$, in each one of said plurality of categories, said average correlation factor, $Y_{cf}$, being applied to any subsequent blood viscosity vs. shear rate profile obtained from a conventional blood viscometer to obtain the circulating blood viscosity.

2. The method of claim 1 wherein said circulating blood viscometer comprises an apparatus that diverts a portion of the circulating blood of the living being out of the living being and subjects the portion to a plurality of shear rates under the influence of a decreasing pressure differential, said diverted portion of the circulating blood being unadulterated.

3. The method of claim 2 wherein said conventional blood viscometer comprises an apparatus that receives an adulterated blood sample from the living being for viscosity analysis.

* * * * *